United States Patent [19]

Mauer

[11] Patent Number: 5,549,116
[45] Date of Patent: Aug. 27, 1996

[54] VEST FOR THE PHYSIOLOGICAL MONITORING OF CHILDREN

[75] Inventor: Mary B. Mauer, Katy, Tex.

[73] Assignee: Texas Children's Hospital, Houston, Tex.

[21] Appl. No.: 512,279

[22] Filed: Aug. 8, 1995

Related U.S. Application Data

[63] Continuation of Ser. No. 218,658, Mar. 28, 1994, abandoned.

[51] Int. Cl.$^6$ .................... A61B 5/402; A41D 1/4
[52] U.S. Cl. .................................. 128/696; 2/102
[58] Field of Search ............................ 128/696, 644, 128/873, 874, 865, 875, 876, 781; 2/48, 49.2, 52, 102, 69, 75, 80, 114, 247, 913; D2/720, 861, 862, 863, 864

[56] References Cited

U.S. PATENT DOCUMENTS

| | | | |
|---|---|---|---|
| D. 260,695 | 9/1981 | Brookfield | D2/190 |
| D. 305,700 | 1/1990 | Werner | D2/864 |
| D. 315,978 | 4/1991 | Scott | D2/183 |
| D. 341,923 | 12/1993 | Kuykendall | D2/830 |
| 3,230,546 | 1/1966 | Sabee | 2/114 |
| 3,952,332 | 3/1975 | Payne | 2/48 |
| 4,108,164 | 8/1978 | Hall, Sr. | 128/781 |
| 4,569,089 | 2/1986 | Neese | 2/108 |
| 4,592,018 | 5/1986 | Wiegman | 355/63 |
| 4,698,848 | 10/1987 | Buckley | 2/114 |
| 4,718,124 | 1/1988 | Sawicki et al. | 2/114 |
| 4,920,969 | 5/1990 | Suzuki et al. | 128/659 |
| 4,926,868 | 5/1990 | Larsen | 128/653 |
| 5,002,270 | 3/1991 | Shine | 272/119 |
| 5,007,472 | 4/1991 | Kuze et al. | 152/546 |
| 5,031,244 | 7/1991 | Inagaki et al. | 2/102 |
| 5,038,779 | 8/1991 | Barry et al. | 128/402 |
| 5,111,818 | 5/1992 | Suzuki | 128/644 |
| 5,195,187 | 3/1993 | Yang | 2/102 |

*Primary Examiner*—Lee S. Cohen
*Attorney, Agent, or Firm*—Arnold, White & Durkee

[57] ABSTRACT

The invention relates to the field of physiological monitoring of ambulatory patients. More specifically, the invention is a vest to be worn by young patients (children) wherein a pouch on the backside of the vest is provided for the placement of a Holter, or similar, physiological monitor. Placement of the monitoring device in this manner makes it difficult for a child to disturb or otherwise manipulate the device. The vest is placed over the child's head and attached via straps that run under the child's arms. In one embodiment, the straps are lengths of material that can be tied in a double-knot, making it difficult for the child to remove the vest. Straps of this design also allow the vest to be easily fitted to children of different sizes. In yet another embodiment, the pouch consists of a series of elastic-like straps. Essential features of this latter embodiment are that the straps hold the physiological monitoring device securely and that the device is substantially inaccessible to the child patient while being worn. The specific arrangement of a back-side pouch that is substantially inaccessible to a child, in combination with the ability to adapt the vest to children of differing sizes provides a stable setup in which high quality physiological data can be obtained from an ambulatory child.

2 Claims, 4 Drawing Sheets

VEST FOR THE PHYSIOLOGICAL MONITORING OF CHILDREN

This application is a continuation of application Ser. No. 08/218,658, filed Mar. 28, 1994, now abandoned entitled Vest For The Physiological Monitoring Of Children.

1. BACKGROUND OF THE INVENTION

Long-term cardiac rhythm assessment of children is often performed via 24 hour ambulatory electrocardiography monitoring (e.g., Holter monitoring). Current techniques to attach a Holter monitor device to an ambulatory child are identical to those used for adult patients: shoulder straps, belts, and jackets. See FIG. 1. The drawbacks with using these techniques on children are multiple. First, these methods present a child with numerous opportunities to manipulate or "fiddle" with the monitoring device. If the monitor is disturbed during a recording session, data acquisition is often interrupted or stopped entirely. In order to prevent this disruption, 24 hour supervision of a child is often necessary. Secondly, these techniques do not allow a small child to maneuver unencumbered, thereby defeating the goal of obtaining data representing the child's heart rhythm during a "normal" day's activities.

Twenty-four hour monitoring of young cardiology patients (e.g., children 0 to 5 years of age) is a routine activity. At the Texas Children's Hospital in Houston, Tex. for instance, approximately 2000 children were monitored in 1993 using 24 hour monitoring.

Due to the problems associated with convincing a small child to carry, and not disturb, a monitoring device for long periods of time, physicians may need to admit the child to a hospital, keeping them for 24 hours so that cardiac rhythm assessment may be performed. Disadvantages of this approach include: (1) the inability to record the child's heart rhythm during "normal" or routine conditions, (2) the expense of a hospital stay, and (3) the inefficient use of hospital resources in having an otherwise healthy child occupy a hospital bed and utilizing medical personnel.

2. SUMMARY OF THE INVENTION

The invention relates to the field of physiological monitoring of ambulatory patients. More specifically, the invention is a vest worn by ambulatory young patients (children) wherein a pouch on the back panel of the vest is provided for the placement of a physiological monitor such as a Holter monitor, an ambulatory blood pressure monitor, a telemetry based monitor, or the like. Placement of the monitoring device in this manner makes it difficult for the young patient to disturb or otherwise manipulate the device. The vest is placed over the child's head and attached via straps that run under the child's arms. In one embodiment, the straps are lengths of material that can be tied in a double-knot, making it difficult for the child to remove the vest. Straps of this design also allow the vest to be easily fitted to children of different sizes. The specific arrangement of a back panel pouch in combination with the ability to adapt the vest to children of differing sizes provides a stable setup in which high quality physiological data can be obtained from an ambulatory child.

3. BRIEF DESCRIPTION OF DRAWINGS

4. DETAILED DESCRIPTION OF A SPECIFIC EMBODIMENT

Figure 1:
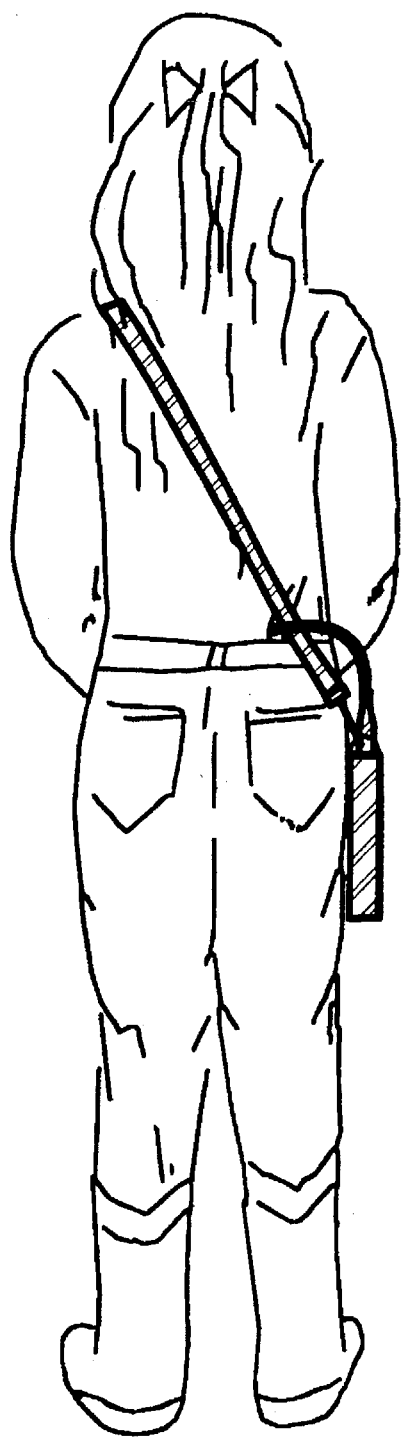
FIG. 1 shows one prior art method of attaching a Holter monitor device to a child.
Figure 2:
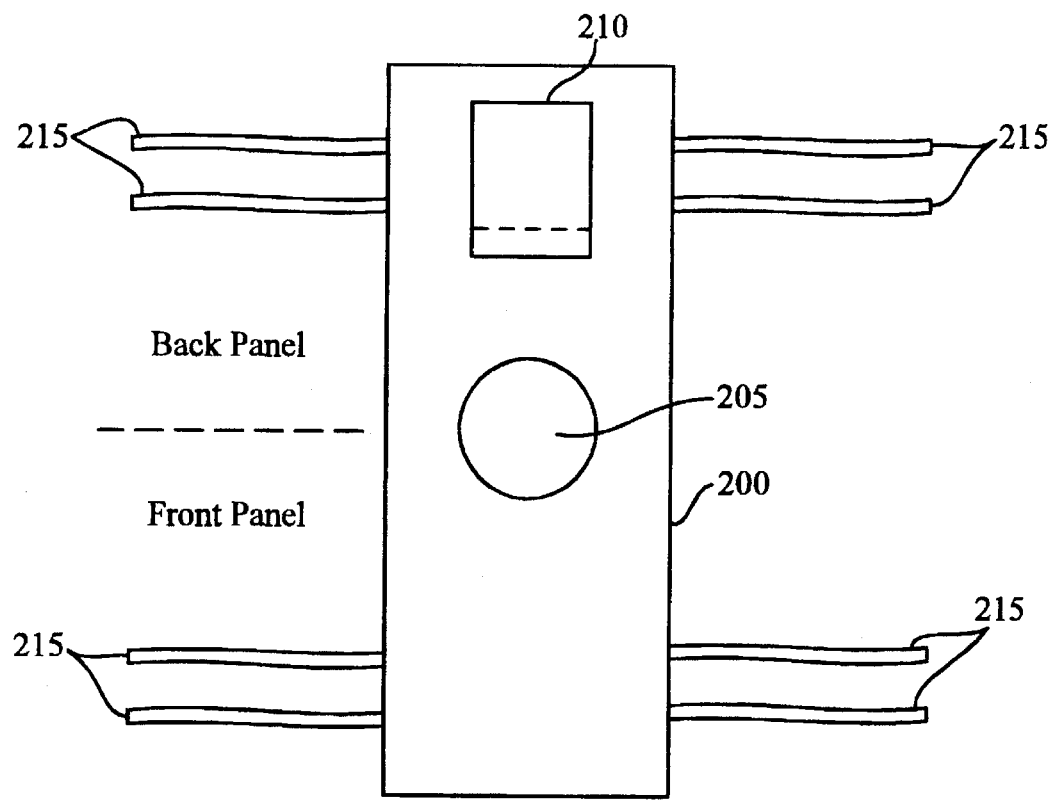
FIG. 2 is a "laid-out" view of the invention.

One illustrative embodiment of the invention is described below as it might be used during 24 hour ambulatory electrocardiography monitoring of a young patient. One example of such monitoring is known as Holter monitoring. As shown in FIG. 2, a vest 200 in accordance with the invention is, essentially, a rectangular piece of cloth with a hole 205 in the middle through which a child's head is passed. When worn, the front panel lies on the child's chest and the back panel on the child's back.

Figure 3:
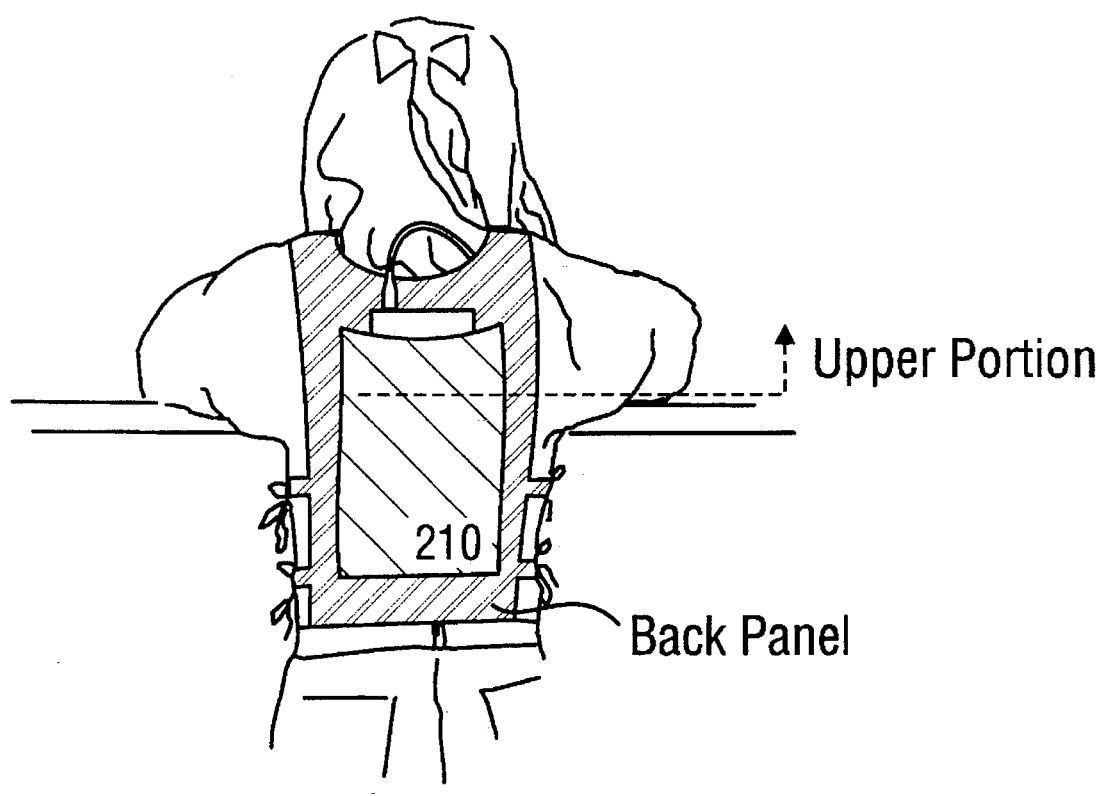
FIG. 3 shows a back view of the invention as worn by a child.

A pouch 210 on the back panel provides a place to store the Holter monitor during use. One benefit of the invention is that by keeping the monitor behind the child, the child is unable to easily disturb or otherwise manipulate the monitor—an important feature for obtaining consistently good quality data from an ambulatory child. As shown in FIG. 3, the pouch's opening is centrally located on the back panel and is in the panel's upper portion—that is, closer to the vest's top relative to the vest's bottom. Since the physiological monitor is substantially inaccessible to the child, it can be kept closed in any reliable manner, e.g., "VELCRO", button, snap, or by a flap. The only requirement for sealing the pouch is that the closure be secure enough to prevent the monitor from slipping out.

Figure 4:
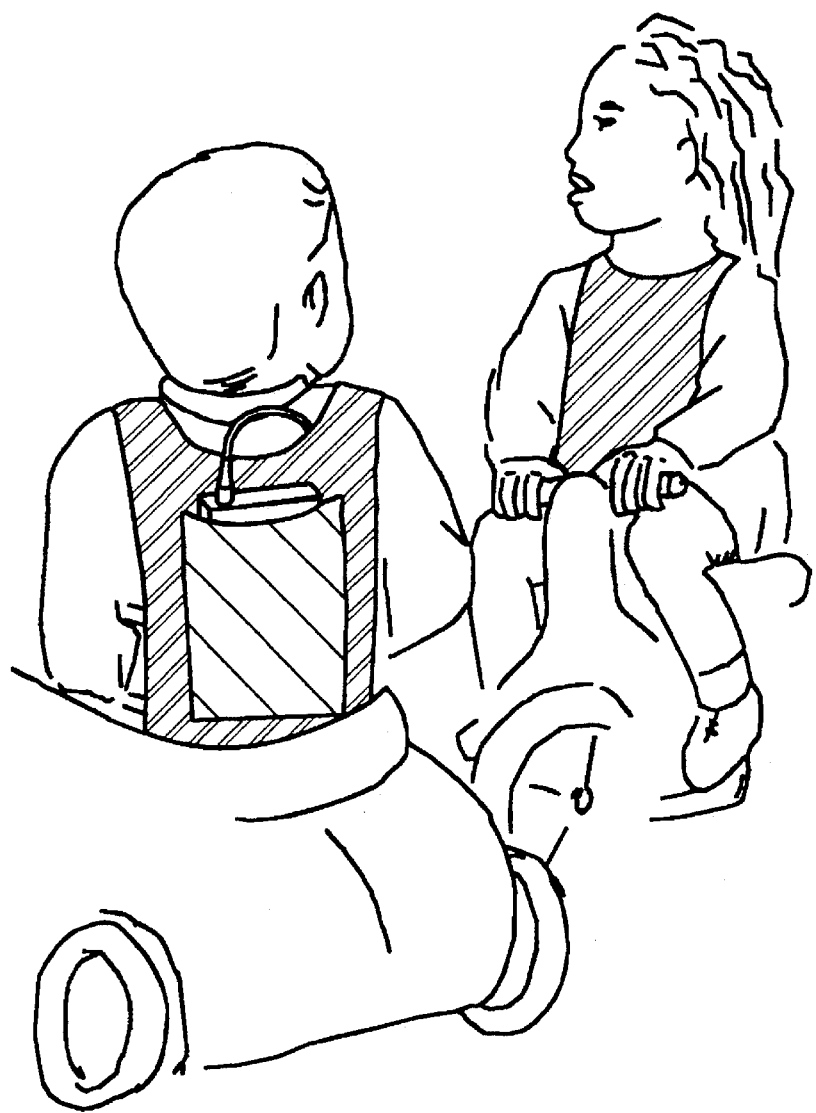
FIG. 4 shows two children wearing one embodiment of the invention. One child is shown from behind, the other from the front.

A series of straps 215 are provided with which to secure the vest to the child. The straps are lengths of material that can be tied in a double-knot thereby making it difficult for the child to remove the vest. FIG. 3 and FIG. 4 shows front and back views of one embodiment of the invention as worn by a child.

In another embodiment of the invention, the pouch is implemented by a series of elastic-like straps. Essential features of this embodiment are that the straps secure the physiological monitoring device to the back panel of the vest and that the device is substantially inaccessible to the child while being worn.

To accommodate children of substantially different sizes the invention can be made in a plurality of sizes. For instance: infant (for children 0 to 1 years of age), toddler (for children 2 to 3 years of age), and child (for children 4 to 5 years of age). Within each age/size range, straps 215 allow the vest to be easily fitted to children of slightly different sizes.

The specific arrangement of a back panel pouch that is essentially inaccessible to a child when being worn, in combination with the ability to adapt the vest to children of differing sizes, provides a stable environment in which high quality physiological data can be obtained from an ambulatory child. Consistently high quality data from children using the invention during 24-hour ambulatory electrocardiography monitoring sessions has been obtained during studies at the Texas Children's Hospital of Houston, Tex.

What is claimed is:

1. A child's vest for carrying a physiological monitoring device, said vest comprising:

(a) a body consisting of an essentially rectangular piece of material forming a front panel and a back panel, said back panel having an upper portion, said body further having a hole centrally located;

(b) a pouch consisting of a plurality of elastic straps for enclosing said physiological monitoring device, said pouch being centrally located in the upper portion of the back panel;

(c) means for securely enclosing said physiological monitoring device in said pouch; and (d) means for adjustably connecting said front panel to said back panel.

2. A method for monitoring a physiological characteristic of a child comprising the steps of:

(a) placing a vest on the child, said vest having a body consisting of an essentially rectangular piece of material forming a front panel and a back panel, said back panel having an upper portion, wherein said back panel has a pouch for enclosing a physiological monitoring device, said pouch being centrally located in the upper portion of the back panel;

(b) placing a physiological monitoring device in said pouch, said physiological monitoring device being capable of measuring said physiological characteristic; and (c) monitoring said physiological characteristic.

* * * * *